United States Patent [19]

Hevey et al.

[11] 4,234,680

[45] Nov. 18, 1980

[54] METHOD FOR TERMINATING A PEROXIDASE CATALYZED REACTION

[75] Inventors: Richard C. Hevey, Rockport, Me.; Mark K. Malmros, Newton, Pa.; Wayne W. Petko, Bound Brook, N.J.

[73] Assignee: Calbiochem-Behring Corp., La Jolla, Calif.

[21] Appl. No.: 63,178

[22] Filed: Aug. 3, 1979

[51] Int. Cl.³ .......................... C12Q 1/66; C12Q 1/28; C12N 9/99

[52] U.S. Cl. .......................................... 435/7; 435/28; 435/184

[58] Field of Search .................... 435/7, 25, 26, 27, 28, 435/184, 192

[56] References Cited

U.S. PATENT DOCUMENTS 4,169,012  9/1979  Dawson et al. .......................... 435/7

*Primary Examiner*—Robert J. Warden
*Attorney, Agent, or Firm*—Natalie Jensen

[57] ABSTRACT

Addition of a low concentration of an alkali metal metabisulfite completely stops color development in a peroxidase-labeled immunoassay wherein the peroxidase catalyzed reaction comprises oxidation of an achromatic substrate to the corresponding chromatic product in the presence of a peroxide.

7 Claims, No Drawings

METHOD FOR TERMINATING A PEROXIDASE CATALYZED REACTION

BACKGROUND OF THE INVENTION

A number of enzyme immunoassays (EIA) have been developed in recent years for the determination of haptens, antigens and antibodies. The basic principle of EIA is predicated on the specific binding between components of a reaction pair (e.g., antigen/antibody, hapten/antibody, etc.) wherein one component is labeled with an enzyme. The accuracy with which the enzyme activity is determined greatly effects the precision and reproducibility of EIA's.

One enzyme frequently used as a label in EIA is horseradish peroxidase. The enzyme is plentiful, inexpensive, and stable and has a high conversion rate of achromatic substrates in the presence of a peroxide to chromatic products which can be measured spectrophotometrically or fluorometrically. One disadvantage of the enzyme, however, is that substrates used to develop colored products in the presence of a peroxide can also be oxidized by air to yield the same colored species. In general, air oxidation of the substrate has an adverse effect on the reproducibility and precision of an EIA using horseradish peroxidase as a label. Although it is possible to correct, via a blank, for autooxidation of the substrate during incubation, a requirement for EIA is that the enzymatic assay be stopped before individual spectrophotometer readings are taken.

To date, investigators working in the field of enzyme immunoassays have employed sulfuric acid or sodium azide as terminating reagents for enzyme immunoassays which utilize a peroxidase label. The foregoing reagents, however, are either corrosive, toxic or pose explosions hazards. An alternative, safe method for terminating EIAs using a peroxidase label would have obvious practical advantages.

DESCRIPTION OF THE INVENTION

The present invention relates to a method for terminating a peroxidase catalyzed reaction. More specifically, the present invention relates to a method of terminating a peroxidase catalyzed reaction employed in a peroxidase-labeled enzyme immunoassay designed to detect and quantitate specific organic materials hereinafter referred to as ligands. According to the present invention, peroxidase catalyzed oxidation of achromatic substrates to the corresponding chromatic products in the presence of a peroxide can be safely and effectively terminated by the addition of an alkali metal metabisulfite.

Specific peroxidase catalyzed reactions which can be terminated according to the instant invention comprise oxidation of substrates selected from the group consisting of o-phenylenediamine, m-phenylenediamine, dianisidine, aniline, p-aminobenzoic acid, and m-aminosalicyclic acid in the presence of a peroxide selected from the group consisting of hydrogen peroxide, methyl peroxide, and ethyl peroxide.

The term "peroxidase-labeled enzyme immunoassay" as used herein refers to an EIA utilizing a peroxidase label. Although the method of termination taught by the instant invention may be generally utilized in any peroxidase-labeled EIA, two classical methodologies wherein termination is readily effected are heterogeneous immunoassays such as the "Sandwich" assay and the competitive binding assay.

The basic components in a peroxidase-labeled Sandwich assay are (1) the ligand to be assayed, (2) insolubilized specific binding substance for the ligand, and (3) peroxidase-labeled specific binding substance for the ligand. The ligand to be assayed is allowed to react with the insolubilized component. Unreacted ligand is then removed and peroxidase-labeled specific binding substance for the ligand is added. Following reaction, unreacted peroxidase-labeled specific binding substance is removed and the enzyme activity of the solid or liquid phase is determined by conversion of a suitable achromatic substrate to the corresponding chromatic product in the presence of a peroxide. Exemplary of the "Sandwich" assay is the detection and quantitation of human IgE.

The basic components in a peroxidase-labeled competitive binding assay are (1) the ligand to be assayed, (2) insolubilized specific binding substance for the ligand and (3) peroxidase labeled ligand. The ligand to be assayed is incubated with a known amount of peroxidase labeled ligand and insolubilized specific binding substance for the ligand. After equilibration, the ligand that is bound to the insolubilized specific binding substance for the ligand is separated from the ligand in solution and the enzymatic activity of the solid or liquid phase is determined in the manner set forth in the preceding paragraph.

The term "peroxidase" as used herein refers to any enzyme exhibiting oxidase or peroxidic activity and includes, but is not limited to, horseradish peroxidase, catalase, tyrosine oxidase and the like. The term "ligand" as used herein refers to antigens, antibodies and haptens. The term "specific binding substance" is any substance or group of substances having a specific binding affinity for the ligand to the exclusion of other substances.

In summary, the present invention relates to a method for terminating a peroxidase catalyzed reaction employed in a peroxidase-labeled enzyme immunoassay for detecting and quantitating ligands, said peroxidase catalyzed reaction comprising the oxidation of a substrate selected from the group consisting of o-phenylendiamine, m-phenylenediamine, dianisidine, aniline, p-aminobenzoic acid and m-aminosalicylic acid in the presence of a peroxide selected from the group consisting of hydrogen peroxide, methyl peroxide and ethyl peroxide, which method comprises adding to the enzyme immunoassay subsequent to the peroxidase catalyzed reaction an amount of alkali metal metabisulfite sufficient to terminate said reaction.

A preferred embodiment of the present invention within the scope of the preceding paragraph relates to terminating a peroxidase catalyzed reaction employed in a peroxidase-labeled heterogenous enzyme immunoassay.

A particularly preferred embodiment within the scope of the preceding paragraph relates to terminating a peroxidase catalyzed reaction wherein said reaction comprises oxidation of a substrate selected from the group consisting of o-phenylenediamine, m-aminosalicylic acid and dianisidine in the presence of hydrogen peroxide.

A further preferred embodiment within the scope of the preceding paragraph relates to terminating a peroxidase catalyzed reaction wherein said peroxidase is horseradish peroxidase.

Although any alkali metal metabisulfite is effective as a terminating agent for the purpose of the present invention, the use of sodium metabisulfite is preferred.

It is preferred the amount of alkali metabisulfite employed be sufficient to provide a concentration of from 0.091 to 0.182 M.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

PREPARATION A

The total IgG fraction of rabbit anti human IgE serum was isolated by a combination of 33% ammonium sulfate precipitation and DEAE cellulose chromatography as described by Garvey et al (1970) in *Methods in Immunology*, pp. 193–98, W. A. Benjamin Inc.

PREPARATION B

Polypropylene tubes were coated with 0.2 ml of a solution of rabbit anti human IgE IgG fraction containing 30 mg/ml IgG in 0.01 M sodium carbonate buffer pH 9.5. The coated tubes were stored at 4° C.

PREPARATION C

Horseradish peroxidase (HRP), 10 mg, was dissolved in 1.0 ml of distilled water and dialyzed overnight at 4° C. against 0.3 M carbonate buffer pH 8.0. Following dialysis 0.46 ml of 0.3 M carbonate buffer was added to the HRP solution to give a final solution containing 5 mg/ml HRP. One percent dinitrofluorobenzene (0.12 ml) was quickly dispensed into the HRP solution and the resulting solution stored for one hour at room temperature. Sodium metaperiodate (0.6 ml of a 0.16 M solution) was subsequently added and the reaction mixture stirred for an additional thirty minutes at room temperature. Ethylene glycol (0.6 ml of a 0.32 M solution) was added and allowed to react for one hour at room temperature. The oxidized HRP was then dialyzed overnight against 0.01 M carbonate buffer.

The IgG fraction of rabbit anti human IgE (1.06 ml of a 4.14 mg/ml solution) was reacted with 2.6 ml of the oxidized HRP for three hours at room temperature and then dialyzed overnight at 4° C. against 0.10 M phosphate buffered saline pH 7.4 containing 4 mM sodium borohydride. The dialyzed conjugate was then redialyzed overnight against 0.10 M phosphate buffered saline pH 7.4 to remove excess sodium borohydride. The enzyme labeled IgG was then subjected to sepharose 6B gel permeation chromatography in order to separate free IgG and HRP from the conjugate.

EXAMPLE I

A suitable number of antibody coated polypropylene tubes were aspirated of their coating solution and washed three times with a solution of 0.85% sodium chloride containing 0.05% Tween-20. A dilution series of IgE Standard (200, 100, 50, 25, 12.5 IU/ml) was prepared in 0.05 M sodium phosphate pH 7.4 buffer containing 0.85% sodium chloride and 0.05% Tween-20 and 0.2 ml of prepared Standard was added to appropriately aspriated and washed IgG coated tubes. The tubes were capped and incubated at 37° C. for three hours. Thereafter, the tubes were aspirated and washed three times with a solution of Tween-20 in normal saline. Horseradish peroxidase (HRP) labeled anti human IgE (0.2 ml) diluted 1:100 in sodium phosphate buffer pH 7.4 containing 0.05% Tween-20, 0.85% sodium chloride and 0.25% bovine serum albumin was subsequently added to each tube. The tubes were then incubated overnight at 4° C. and subsequently aspirated and washed three times with Tween-20/NaCl.

The amount of HRP labeled anti human IgE (conjugate) bound to the tubes was determined by adding 1.0 ml of 0.033 M sodium phosphate buffer pH 6.6 containing 5.4 mM o-phenylenediamine dihydrochloride and 1.6 mM hydrogen peroxide at timed intervals. Following a thirty minute incubation period, 0.10 ml of 2 M sodium metabisulfite was added in the same timed sequence and the contents of the tubes were rapidly mixed to stop the reaction. The optical density (O.D.) of each solution was then measured at 450 nm. In order to verify that the enzymatic reaction had ceased and that the O.D. did not increase or decrease with time, each solution was reread at timed intervals for two hours. Following quenching or termination, very little change in optical density was observed over the two-hour time interval. The dose response curve (i.e., O.D. vs. IgE concentration IU/ml for the assay was linear up to 100 IU/ml IgE.

EXAMPLE II

In order to determine the minimum concentration of sodium metabisulfite required for termination, aqueous sodium metabisulfite was prepared in concentrations of 2.0 M and 1.0 M. An assay solution containing 5.4 mM o-phenylenediamine dihydrochloride and 1.6 mM hydrogen peroxide in 33 mM sodium phosphate buffer pH 6.6 was also prepared. The enzyme reaction was initiated by the addition of $5\mu$ 1 of horseradish peroxidase labeled anti human IgE to 1.0 ml of the assay solution. After an appropriate time interval, 0.1 ml of 1 M sodium metabisulfite was added to the reaction mixture. Following the addition, the O.D. of the solution was read at periodic intervals for one hour in order to verify that termination had occurred. By repeating the procedure using 0.01 ml of 1 M sodium metabisulfite, 0.1 ml of 2 M sodium metabisulfite and 0.01 ml of 2 M sodium metabisulfite, it was established that 0.1 ml of 1 M sodium metabisulfite was sufficient to instantaneously terminate the enzymatic reaction. Accordingly, a concentration of 0.091 M sodium metabisulfite in the final assay solution is sufficient to terminate the enzymatic reaction.

During the course of the foregoing investigation, it was observed that when 1 M aqueous sodium metabisulfite was used to terminate the enzymatic reaction an enhancement of color yield (O.D.) occurred.

EXAMPLE III

The following experiment was conducted in order to determine the effect of pH on quenching with sodium metabisulfite. An assay solution containing 5.4 mM o-phenylenediamine dihydrochloride and 1.6 mM hydrogen peroxide in 0.33 M sodium phosphate/citric acid buffer pH 5.4 was prepared. Horseradish peroxidase labeled anti human IgE ($5\mu$ 1) was added to 1.0 ml of the assay solution in order to initiate the enzymatic reaction. After an appropriate time interval, 0.1 ml of 2 M sodium metabisulfite in 1.03 M phosphate buffer pH 5.35 was added to the solution to terminate the reaction. The solution was read at five minute intervals for one hour following termination. No variation in O.D. was observed.

During the course of the foregoing experiment, it was observed that the color enhancement noted in Example II was eliminated. Since it is known that the color yield (O.D.) of the peroxidase catalyzed reaction of o-phenylenediamine is pH dependent (i.e., the extinction coefficient of the product of the reaction is pH dependent), the elimination of color enhancement in the more buffered system of the instant example is expected.

EXAMPLE IV

The procedure of Example II was repeated utilizing the following assay solutions:
(1) 2.6 mM m-aminosalicylic acid and 1.6 mM phosphate buffer pH 6.2; and
(2) 0.34 mM dianisidine and 3.2 mM hydrogen peroxide in 100 mM phosphate buffer pH 6.0.

The optical density (O.D.) in each case was determined at 460 nm.

In order to maintain the final pH of the assay systems at 6.0, termination was effected with 1 M sodium metabisulfate prepared in 0.5 M phosphate buffer titrated to pH 6 with sodium hydroxide. Assay systems employing m-aminosalicylic acid and dianisidine were effectively terminated with 0.1 ml of 1 M sodium metabisulfite.

The invention being thus described, it will be obvious that the same may be varied in many ways. Such variations are not to be regarded as a departure from the spirit and scope of the invention, and all such modifications are to be included within the scope of the following claims.

What is claimed is:

1. A method for terminating a peroxidase catalyzed reaction employed in a peroxidase-labeled enzyme immunoassay for detecting and quantitating ligands, said peroxidase catalyzed reaction comprising the oxidation of a substrate selected from the group consisting of o-phenylenediamine, m-phenylenediamine, dianisidine, aniline, p-aminobenzoic acid and m-aminosalicylic acid in the presence of a peroxide selected from the group consisting of hydrogen peroxide, methyl peroxide and ethyl peroxide, which method comprises adding to the enzyme immunoassay subsequent to the peroxidase catalyzed reaction an amount of alkali metal metabisulfite sufficient to terminate said reaction.

2. A method according to claim 1 wherein said peroxidase-labeled enzyme immunoassay is a heterogeneous assay.

3. A method according to claim 2 wherein said peroxidase catalyzed reaction comprises oxidation of a substrate selected from the group consisting of o-phenylenediamine, m-aminosalicylic acid and dianisidine in the presence of hydrogen peroxide.

4. A method according to claim 3 wherein said peroxidase is horseradish peroxidase.

5. A method according to claim 4 wherein the alkali metal metabisulfite is sodium metabisulfite.

6. A method according to claim 5 wherein said heterogeneous assay is a sandwich assay for detecting and quantitating human IgE.

7. A method according to claim 1 wherein the amount of alkali metabisulfite employed is sufficient to provide a concentration of from 0.091 to 0.182 M.

* * * * *